United States Patent [19]

Yamada et al.

[11] Patent Number: 4,683,048
[45] Date of Patent: Jul. 28, 1987

[54] METHOD OF MANUFACTURING ION SELECTIVE ELECTRODE PAIR

[75] Inventors: Sadao Yamada; Takeshi Takayama; Osamu Seshimoto; Akira Yamaguchi, all of Asaka, Japan

[73] Assignee: Fuji Photo Film Co., Ltd., Kanagawa, Japan

[21] Appl. No.: 734,974

[22] Filed: May 16, 1985

[30] Foreign Application Priority Data

May 18, 1984 [JP] Japan ............................. 59-100317

[51] Int. Cl.[4] .......................................... G01N 27/46
[52] U.S. Cl. .................................. 204/416; 204/418; 204/419; 83/875
[58] Field of Search ............................ 204/416–420; 83/875; 422/55, 100

[56] References Cited

U.S. PATENT DOCUMENTS

| 4,053,381 | 10/1977 | Hamblen et al. | 204/418 |
| 4,083,390 | 4/1978 | Ingham | 83/875 |
| 4,214,968 | 7/1980 | Battaglia et al. | 204/435 |
| 4,243,082 | 1/1981 | Paris et al. | 83/875 |
| 4,528,085 | 7/1985 | Kitajima et al. | 204/419 |

Primary Examiner—T. Tung
Attorney, Agent, or Firm—Jules E. Goldberg

[57] ABSTRACT

A conductive layer is formed on an insulating base, and at least one groove is formed in the conductive layer by cutting a part of the material of the conductive layer so that the conductive layer is divided into at least a pair of portions electrically isolated from each other by the cut groove. Thereafter, an ion selective layer is formed on the conductive layer to cover substantially the entire surface of the conductive layer including the cut groove.

9 Claims, 7 Drawing Figures

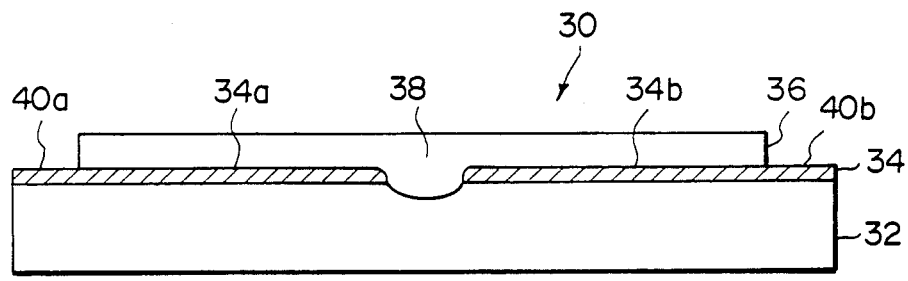
F I G. 1
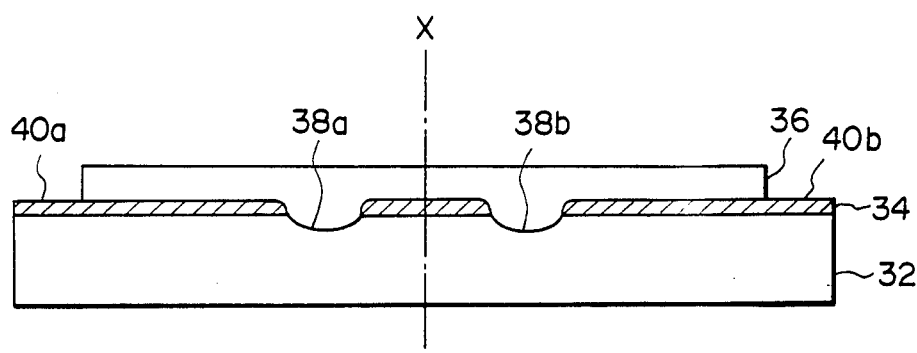
F I G. 2
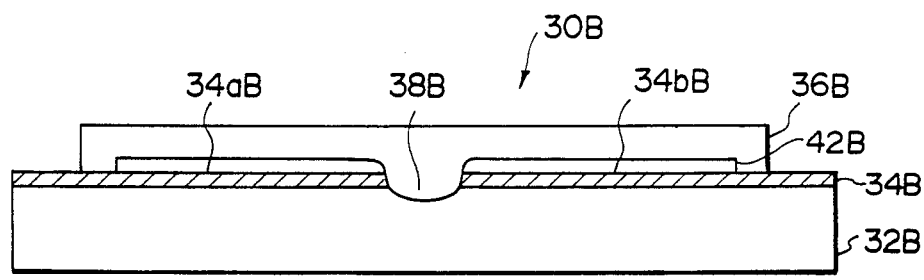
F I G. 3

METHOD OF MANUFACTURING ION SELECTIVE ELECTRODE PAIR

BACKGROUND OF THE INVENTION

1. Field of the Invention

This invention relates to an ion selective electrode pair for potentiometrically measuring ionic activity or ionic concentration of a specific ion in an aqueous liquid sample such as blood, urine, saliva or other body fluid, and also relates to a method of manufacturing an ion selective electrode pair.

2. Description of the Prior Art

In U.S. Pat. Nos. 4,053,381 and 4,214,968, Japanese Unexamined Patent Publication No. 57(1982)-17851 and Japanese Unexamined Patent Publication No. 58(1983)-156848 (GB 2121183 A), there is disclosed a planar film-like dry type ion selective electrode pair to be incorporated in an ionic activity measuring instrument for potentiometrically measuring ionic activity or concentration of a specific ion contained in aqueous liquid samples such as body fluid (e.g. blood including whole blood, serum and plasma; lymph; saliva; cerebrospinal fluid; vaginal liquid; urine), liquors, waste water, and stream water using a very small amount (sessile drop amount) of such samples.

The film-like ion selective electrode pair disclosed in Japanese Unexamined Patent Publication No. 58(1983)-156848 is especially epoch-making in that electrical insulation between a pair of ion selective electrodes can be easily established and accordingly the ionic activity measuring instrument using the ion selective electrode pair can be reduced in size.

The ion selective electrode pair, utilizing the fact that the ion selective layer of the ion selective electrode pair is substantially an insulator, is formed by providing a V-shaped groove on a metal conductive layer before superposing the ion selective layer by scribing with a sharp cutting edge having a wedge-shaped cross section, so that the metal conductive layer is divided into a pair of portions insulated from each other, each forming an electrode. With this arrangement, a very compact ion selective electrode pair can be easily produced. However, it is very difficult to completely remove metal cuttings produced by scribing from the V-shaped groove, and when the metal cuttings mingle in the upper layers, sufficient electrical insulation cannot be maintained, thereby producing a defective product. Further, since scribing is inherently an operation to push the metal layer aside, there arise various problems.

FIG. 7 is an enlarged fragmentary cross-sectional view showing the V-shaped groove. In FIG. 7, reference numeral 10 denotes an ion selective electrode pair. The ion selective electrode pair 10 is formed by laminating a silver layer 14, a silver halide layer 16 and an ion selective layer 18 in this order on an insulating base 12. Reference numeral 20 denotes a groove having a V-shaped cross section formed by scribing the silver layer 14 to divide it into a pair of insulated portions each forming an electrode. In order to obtain a good electrical insulation between the electrodes, the depth of the V-shaped groove 20 should reach the insulating base 12 through the silver layer 14, and thus, the portion of the silver layer 14 and the insulating base 12 forced aside by the cutting edge forms a raised portion 22 on each side of the V-shaped groove 20. This is disadvantageous in that, in order to cover the silver layer 14 at the raised portion 22, the thickness of the ion selective layer 18, which is of expensive material, must be increased so that the manufacturing cost of the ion selective electrode pair is increased. Further, when the ion selective electrode pair is incorporated in an ionic activity measuring instrument, the ion selective electrode pair cannot be brought into close contact with a mask on which is mounted a porous bridge and which covers the surface of the electrode pair except the portions on which sample liquid and reference liquid are deposited. Further, since the V-shaped groove 20 is formed deep into the insulating base 12, the insulating base 12 is apt to be deformed.

SUMMARY OF THE INVENTION

In view of the foregoing observations and description, the primary object of the present invention is to provide a dry type ion selective electrode pair which is compact and can be brought into close contact with a mask for covering the surface of the electrode pair, and in which high electrical insulation between the pair of electrodes or half cells can be ensured and the insulating base is not apt to be deformed.

Another object of the present invention is to provide a method of manufacturing such a dry type ion selective electrode pair with ease and at low cost.

The ion selective electrode pair in accordance with the present invention comprises a conductive layer and an ion selective layer formed on an insulating base in this order, the conductive layer being divided into at least two portions electrically isolated from each other by a cut groove which is formed by mechanically cutting a part of the material of the conductive layer, and the cut groove being covered with the ion selective layer.

In accordance with the method of the present invention, a conductive layer is first formed on an insulating base, and at least one groove is formed in the conductive layer by cutting a part of the material of the conductive layer so that the conductive layer is divided into at least a pair of portions electrically isolated from each other by the cut groove. Thereafter, an ion selective layer is formed on the conductive layer to cover substantially the entire surface of the conductive layer including the cut groove.

BRIEF DESCRIPTION OF THE DRAWINGS

FIG. 1 is a schematic cross-sectional view an ion selective electrode pair in accordance with a first embodiment of the present invention, FIG. 2 is a schematic cross-sectional view of a modification of the ion selective electrode of FIG. 1, FIG. 3 is schematic cross-sectional view of an ion selective electrode pair in accordance with a second embodiment of the present invention.

DESCRIPTION OF THE PREFERRED EMBODIMENT

Figure 4:
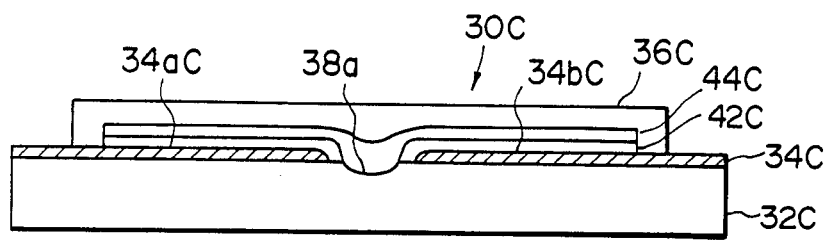
FIG. 4 is a schematic cross-sectional view of an ion selective electrode pair in accordance with a third embodiment of the present invention.

In FIG. 1, an ion selective electrode pair 30 in accordance with an embodiment of the present invention comprises an insulating base 32, a conductive layer 34 and an ion selective layer 36. A cut groove 38 is formed in the conductive layer 34 to divide it into a pair of electrically insulated portions 34a and 34b. The cut groove 38 is formed by mechanically cutting the conductive layer 34 with, for instance, a cutting tool after the conductive layer 34 is formed on the insulating base 32 and before the ion selective layer 36 is formed thereon. The depth of the cut groove 38 need only be sufficient to electrically insulate the portions 34a and 34b from each other. However, it is preferred that the cut groove 38 reach the insulating base 32 and a part of the insulating base 32 be cut away in order to ensure a sufficient insulation between the portions 34a and 34b, though it is preferred that the depth of the cut groove 38 be selected so as not to affect the flatness of the insulating base 32. The depth of the portion of the cut groove 38 in the insulating base 32 should be not larger than 20 microns and preferably should be not larger than 15 microns.

The width of the cut groove 38 may be of any magnitude insofar as it is sufficient to assure that the electrical insulation between the portions 34a and 34b of the conductive layer 34 can be maintained. As a practical matter, since the cut groove 38 is formed by peeling off the conductive layer 34 by a cutting tool, its width is generally not smaller than 0.3 mm. However, reduction of the width of the cut groove 38 to less than 0.3 mm does not substantially contribute to reduction in the overall size of the ion selective electrode pair 30.

Basically, though the cut groove 38 may be formed in any position in the conductive layer 34, the groove 38 should at least be located at an area which ensures an area generating an electro-motive force (potential) when one of the portions 34a and 34b of the electrode layer 34 is brought into contact with a sample liquid.

Exposed areas 40a and 40b of the conductive layer 34 which function as a terminal for electrical connection are provided at respective sites in which such a surface area is ensured. If electrical contact with the conductive layer 34 is achieved by piercing with a needle-like probe or the like, the exposed areas 43a and 43b are not required.

As the cutter for cutting the cut groove 38, a slotter tool bit, a fluting tool bit, a cutting-off cutter or the like can be used. Preferably, the cutting tool has a semispherical tip the diameter of which is 1 to 4 mm (preferably 2 to 3.5 mm) or a U-shaped tip having a width of 1 to 4 mm (preferably 2 to 3.5 mm), though it may instead have an angular tip. As the material of the cutting tool, various known materials can be used. For example, high speed steel, cemented carbide, ceramic or the like may be used.

After the conductive layer 34 is separated into two portions 34a and 34b or a pair of half cells, the ion selective layer 36 is coated over the entire area of the conductive layer 34 except the exposed portions 40a and 40b. (The portions 34a and 34b will be sometimes referred to as "half cells", and the exposed portions 40a and 40b of the conductive layers 34 will be sometimes referred to as "terminals", hereinbelow.) The ion selective layer 36 is also coated over the cut groove 38. The ion selective layer 36 has a high electrical resistance and therefore the insulation between the half cells 34a and 34b established by the cut groove 38 is further enhanced. Cuttings produced during machining of the cut groove 38 can be easily removed before the ion selective layer 36 is coated on the conductive layer 34, and accordingly there is little possibility that cuttings of the conductive layer material will get into in the ion selective layer 36 to degrade the insulation between the half cells 34a and 34b.

The ion selective electrode pair thus obtained has a pair of electrodes or half cells 34a and 34b which are electrochemically equivalent to each other, and can be produced very easily since electrical insulation between the pair of half cells 34a and 34b is established by mechanically cutting the conductive layer 34. Further since the groove 38 is formed by cutting and removing a part of the conductive layer material, the conductive material is not raised on opposite sides of the cut groove 38 and accordingly, the expensive ion selective layer 36 may be small in thickness, whereby the ion selective electrode pair can be manufactured at low cost. Further, since there is no raised portion formed on opposite sides of the groove for electrically insulating the electrodes from each other, the surface of the ion selective electrode pair can be flattened, whereby contact of the ion selective electrode pair with a mask in which a liquid feed opening is formed can be improved. The cut groove 38 may be relatively shallow, and accordingly there is little fear of deformation of the insulating base 32.

The ion selective electrode pair 30 shown in FIG. 1 can be used as a single electrode or a half cell. In this case, one of the portions 34a and 34b divided by the cut groove 38, for instance the portion 34b, may be made smaller and the exposed portion or the terminal 40b on the portion 34b can be eliminated.

As shown in FIG. 2, a pair of electrochemically equivalent half cells can be simultaneously produced by forming two cut grooves 38a and 38b symmetrically at two portions and cutting the ion selective electrode pair 30A thus obtained along line X—X at the middle between the grooves 38a and 38b after the ion selective layer 36 is formed.

In the ion selective electrode pair comprising a conductive layer and an ion selective layer formed on an insulating base in this order like the ion selective electrode pair shown in FIG. 1, the conductive layer may comprise a compound of inert conductive material and redox couple, for instance. As the inert conductive material, those which do not electrochemically react with the redox couple, e.g., graphite, platinum and gold, can be used, with graphite being preferred. As the redox couple, ferric iron ion/ferrous ion couple such as $Fe(CN)_6^{3-}/Fe(CN)_6^{4-}$ or primary cobalt ion/secondary cobalt ion couple such as $Co(terpyridyl)_2^{3+}/Co(terpyridyl)_2^{2+}$ can be used. Such a mixed layer of the redox couple and the inert conductive material can be formed in accordance with known art described in Japanese Patent Publication No. 58(1983)-4981, for example.

The ion selective electrode pair 30B shown in FIG. 3 in accordance with another embodiment of the present invention comprises a conductive metal layer 34B, a layer 42B of a water-insoluble salt of the metal forming the conductive metal layer 34B and an ion selective layer 36B formed on an insulating base 32B in this order. A cut groove 38C is formed to skive a part of the conductive metal layer 34B and the layer 42B of the water-insoluble salt before the ion selective layer 34B is applied on the layer 42B of the water-insoluble salt. The cut groove 38C may be formed in the same manner as described above in conjunction with the embodiment shown in FIG. 1. For example, the conductive metal layer 34B may be of silver and the water-insoluble salt layer 42B may be of a silver halide. The silver layer 34B and the silver halide layer 42B may be formed by oxidative-halogenation treatment after deposition of silver as described in Japanese Unexamined Patent Publication No. 58(1983)-156848. The oxidative-halogenation may be effected either before or after formation of the cut groove 38C. The redox couples described above in conjunction with the embodiment shown in FIG. 1 may be employed instead of the water-insoluble salt, and the inert conductive materials also described above may be employed as the material for the conductive metal layer 34B.

FIG. 4 shows an ion selective electrode pair in accordance with a third embodiment of the present invention. The ion selective electrode pair 30C of this embodiment comprises a metal layer 34C, a water-insoluble salt layer 42C composed of a water-insoluble salt of the metal forming the conductive metal layer 34C, a water-soluble salt layer 44C composed of a water-soluble salt having an anion in common with the salt forming the water-insoluble salt layer 42C and an ion selective layer 36C formed on an insulating base 32C in this order. As in the first and second embodiments, a cut groove 38C is formed to divide the conductive metal layer 34C into two portions 34aC and 34bC before the ion selective layer 36C is coated on the water-soluble salt layer 44C. For example, the conductive metal layer 34C may be composed of silver, the water-insoluble salt layer 42C may be composed of AgCl and the water-soluble salt layer 44C may be composed of KCl. In this case, the ion selective layer 36C may be, for instance, a polymer matrix film containing valinomycin which is $K^+$ ion selective. In this case, the ion selective electrode pair 30C may be used for measuring ion activity of $K^+$ ion. The oxidative-halogenation after deposition of silver may be effected either before or after formation of the cut groove 38C, though in the third embodiment shown in FIG. 4, the oxidative-halogenation is effected after formation of the cut groove 38C.

Figure 5:
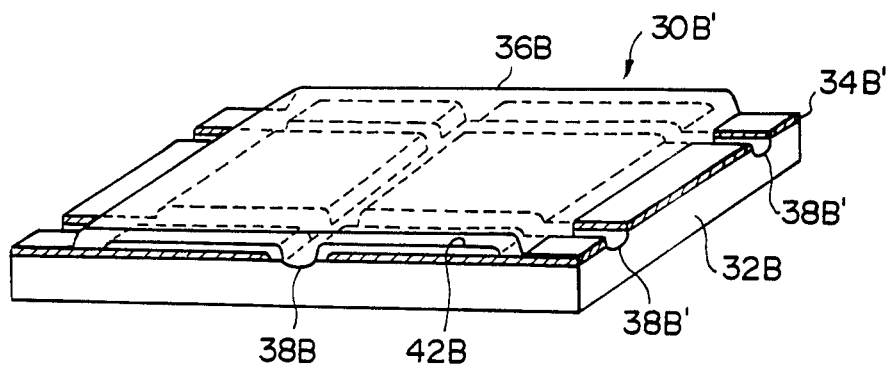
FIG. 5 is a schematic perspective view of a preferred modification of the embodiment shown in FIG. 3.
Figure 6:
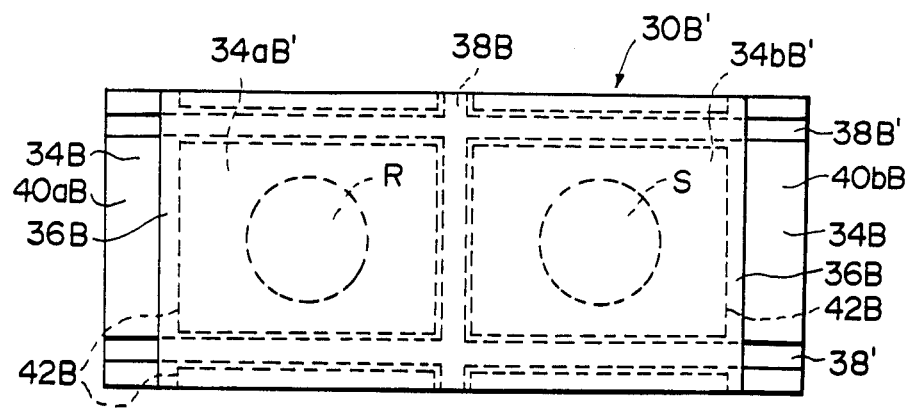
FIG. 6 is a schematic plan view of the ion selective electrode pair of FIG. 5.
Figure 7:
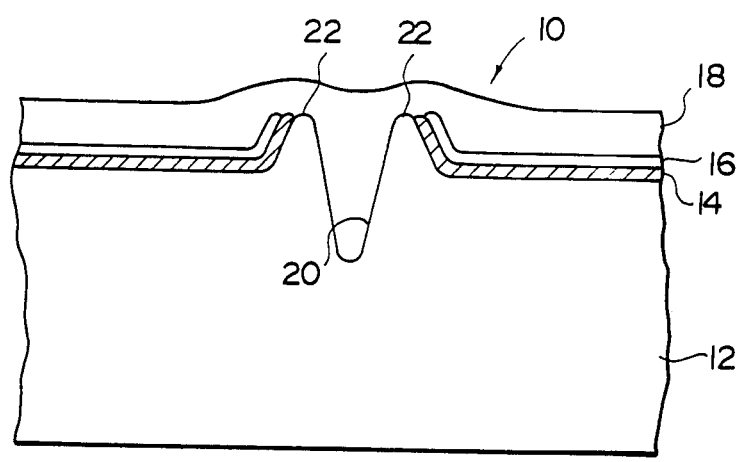
FIG. 7 is a schematic fragmentary cross-sectional view of an ion selective electrode pair in accordance with the prior art.

In the ion selective electrode pairs 30, 30B and 30C, the conductive layer (34, 34B, 34C) is divided into two portions (34a, 34b; 34aB, 34bB; 34aC, 34bC) electrically isolated from each other by forming at least one cut groove (38, 38B, 38C) in the conductive layer to extend in the transverse direction thereof. The electrical insulation between the two portions or two half cells can be further enhanced by further providing at least two longitudinal cut grooves in the conductive layer as shown in FIGS. 5 and 6. FIGS. 5 and 6 show a preferred modification of the embodiment shown in FIG. 3. The ion selective electrode pair 30B' shown in FIGS. 5 and 6 is substantially the same as that shown in FIG. 3 except that a pair of longitudinal cut grooves 38B' are formed in the conductive layer 34B so that each of the portions 34aB' and 34bB' of the conductive layer 34B or each of the half cells is surrounded by the cut groove except the side of the terminal 40aB or 40bB. This arrangement further enhances the insulation of the half cells. Therefore, even if sample liquid and reference liquid deposited on the half cells at portions indicated at S and R flows out to the periphery of the respective half cells, short circuiting cannot occur. It should be noted that FIGS. 5 and 6 are scaled in the longitudinal direction of the conductive layer (the horizontal direction in the figures) more than in the transverse direction of the same and sample liquid and reference liquid respectively deposited on the portions S and R cannot be brought into direct contact with each other on the ion selective layer 36B. Connection between the liquids on the portions S and R is achieved by way of a porous or capillary bridge.

The ion selective electrode pair of the present invention can be formed of known materials conventionally employed in forming ion selective electrodes.

As the insulating base, various known materials can be used provided that they can support the layers formed thereon and they are electrically insulating and inert, though film-forming polymers such as polyethylene terephthalate are preferred as described in Japanese Unexamined Patent Publication No. 58(1983)-156848. Further, the thickness of the insulating base is preferably 50 to 500 μm.

As the conductive layer, conductive metals used for known electrodes, conductive metal oxides such as those described in Per Kofstad "Nonstoichiometry, Diffusion and Electrical Conductivity in Binary Metal Oxides", New York, Willy-Interscience, 1972, and graphite can be used. As the conductive metals for the conductive layer, silver, platinum, palladium, gold, nickel, copper, aluminum, indium and the like are preferred. As the conductive metal oxides for the conductive layer, tin oxide, indium oxide, zinc oxide, a mixture of tin oxide and antimony oxide, and a mixture of tin oxide and indium oxide are preferred.

The conductive layer may be formed by known methods such as vacuum deposition, chemical plating and the like. Further, the conductive layer may be formed by applying conductive metal powder, conductive metal oxide powder or graphite (carbon powder) on an insulating base using a binder in accordance with the disclosures of Japanese Unexamined Patent Publication No. 58(1983)-156848 or U.S. Pat. No. 4,214,968. In order to mass-produce the ion selective electrode pair of the present invention, it is preferred that the conductive layer be formed on an insulating base in a striped pattern as described in Japanese Unexamined Patent Publication No. 58(1983)-10645 (GB 2102963 A). Preferably, the thickness of the conductive layer thus formed is 50 nm to 50 μm.

When at least one of the conductive metal and the conductive metal oxide is used as the conductive layer, the water-insoluble salt layer to be formed on the conductive layer may be formed by a known method. In Japanese Unexamined Patent Publication No. 58(1983)-156848 (GB 2121183 A) and U.S. Pat. No. 4,437,970, and Japanese Patent Publication No. 58(1983)-4981, there is disclosed a method of forming a water-insoluble metal halide layer on a metal layer by oxidative-halogenating the metal layer. The thickness of the water-insoluble salt layer should generally be 50 nm to 10 μm, and preferably should be 50 nm to 1 μm.

When the conductive layer is to be provided with an electrical connecting terminal at each end, each portion of the conductive layer at which the terminal is to be formed is masked. Such masking of the conductive layer can be effected by a known method described in Japanese Unexamined Patent Publication Nos. 58(1983)-156848 and 58(1983)-211648.

The water-soluble salt layer (an electrolyte layer) formed on the water-insoluble salt layer and having an anion in common with the water-insoluble salt layer may be formed by any known method. For example, the electrolyte layer or the water-soluble salt layer may be formed in accordance with the method described in Japanese Patent Publication No. 58(1983)-4981, U.S. Pat. No. 4,214,968 and Japanese Unexamined Patent Publication No. 57(1982)-17852.

The ion selective layer is a layer which has a selective response to a specific ion, and has a high electrical resistance of such a level as to be substantially an insulator in the dry state before being brought into contact with a sample liquid or a reference liquid. In this specification, the term "selective response to a specific ion" should be interpreted to include not only the properties of being permeable only to a specific ion or being responsive only to a specific ion, but also the properties of being able to select a specific ion from other materials with a time difference sufficient for measurement. Further, where a potentiometric response corresponding to the change in ionic activity in a liquid is measured through ion exchange so that a function the same as that of selective response to a specific ion is obtained, this should be interpreted as exhibition by the layer of "selective response to a specific ion".

Since the sample liquid and the reference liquid are both aqueous in the present invention, the ion selective layer must be water-insoluble, though it may be either hydrophilic or hydrophobic. It is preferred that the ion selective layer be hydrophobic.

Also the ion selective layer can be formed by any known method. For example, ion carrier is dissolved in ion carrier solvent and hydrophobic organic binder is added thereto. The solution thus obtained is coated on the water-insoluble salt layer, the electrolyte or the conductive layer, and dried. Generally, the concentration of the ion carrier is about 0.05 to 10 g/m$^2$, and the thickness of the ion selective layer is generally about 3 $\mu$m to about 125 $\mu$m, and preferably 5 $\mu$m to 50 $\mu$m. As the ion carrier, there can be used valinomycin, cyclic polyethers, tetralactone, macrolide actins, enniatins, monensin, gramicidins, tetraphenyl borate, cyclic polypeptides and the like. The ion carrier, ion carrier solvent, hydrophobic organic binder and formation of the ion selective layer are discussed in detail in Japanese Unexamined Patent Publication No. 58(1983)-156848, Japnese Patent Publication No. 58(1983)-4981, U.S. Pat. Nos. 4,053,381, 4,171,246 and 4,214,968, and "Research Disclosure", No. 16113 (September 1977).

As the material for the ion selective layer, an ion exchange material can also be used. In this case, potentiometric response due to change in ion activity in the ion containing solution resulting from ion exchange effect of the ion exchange material is measured. The ion exchange materials suitable for the present invention and a method of forming the ion selective layer using the ion exchange materials are described in detail in U.S. Pat. No. 4,115,209.

When the ion to be measured is K$^+$, Na$^+$, Ca$^{2+}$, HCO$_3^-$ or CO$_3^{2-}$, the ion selective layer is essential. However, when the ion to be measured is Cl$^-$ and the ion selective electrode pair comprises a silver layer (as the conductive metal layer) and a silver chloride layer (as the water-insoluble salt layer), a protective layer permeable to the ion to be measured can be used in place of the ion selective layer. The protective layer can be formed of various materials described in U.S. Pat. Nos. 4,199,411 and 4,199,412 and Japanese Unexamied Patent Publication Nos. 53(1978)-72622 and 54(1979)-1384, e.g. cellulose esters or latex. In this specification, such protective layer should be interpreted to be an ion selective layer.

When redox couple is used for forming the conductive layer and the ion selective layer, a known method can be utilized. For example, redox couple compositions and a method suitable for forming the conductive layer and the ion selective layer are described in U.S. Pat. Nos. 4,053,381 and 4,214,968.

When measuring the ion activity of an ion using the ion selective electrode pair of the present invention, the ion selective electrode pair is covered with a mask provided with a pair of openings through which the sample liquid and the reference liquid are dropped onto depositing portions on the respective half cells. The depositing portions are electrically connected by way of a bridge and the conductive layers of the respective half cells are connected by way of a potentiometer. Then the sample liquid and the reference liquid are deposited onto the depositing portions and the potential difference between the pair of half cells is read. This method of measuring ion activity is known and is disclosed in, for instance, U.S. Pat. Nos. 4,053,381 and 4,184,936. Further, by preparing ion selective electrode pairs for various ions in accordance with the present invention, the ion activity of various ions can be simulataneously measured according to the method which the inventors of this invention previously proposed in Japanese Unexamined Patent Publication No. 58(1983)-211648 and Japanese Patent Application No. 59(1984)-11744.

The present invention will be described in more detail with reference to several examples.

EXAMPLE 1

Silver was vacuum-deposited onto a first set of 200 PET (polyethylene terephthalate) sheets to a thickness of 400 nm, onto a second set of 200 PET sheets to a thickness of 600 nm and onto a third set of 200 PET sheets to a thickness of 800 nm. The thickness of the PET sheets was 188 $\mu$m. Half of the PET sheets bearing thereon the silver layer of each thickness were provided with a scribed groove formed by scribing the silver layer with a cutter knife (NT cutter-A-300 model, Nippon Tenshashi K.K.) (according to the prior art disclosed in Japanese Unexamined Patent Publication No. 58(1983)-156848), and the other half of the PET sheets bearing thereon the silver layer of each thickness were provided with a cut groove formed by mechanically cutting the silver layer with a U-shaped cutting tool having a width of 5 mm (according to the present invention). The scribed grooves were all about 30 $\mu$m in depth (at the deepest portion) and the cut grooves were all about 10 $\mu$m in depth. The material was raised on opposite sides of the scribed groove by about 20 $\mu$m. In the case of the sheets provided with the scribed groove, one or two of the sheets bearing thereon the silver layer of each thickness exhibited electrical connection between the two portions of the silver layer divided by the groove, while in the case of the sheets provided with the cut groove in accordance with the present invention, none of the sheets exhibited electrical connection between the two portions of the silver layer divided by the groove.

Through a microscope, a high raised portion was viewed on each side of the groove and a deep cut in the PET film was viewed in the case of the sheets provided with the scribed groove, while scaresly any raised portion was viewed on opposite sides of the groove in the case of the sheets provided with the cut groove.

EXAMPLE 2

Silver was vacuum-deposited onto a 188 μm thick PET film to form a silver layer of about 800 nm, and liquid resist containing as its major component polyvinyl chloride (described in Japanese Unexamined Patent Publication No. 58(1983)-102146) was coated on the end portions of the silver layer over a width of 5 mm each and dried to form thereon polymeric films, thereby masking the end portions of the silver layer to protect them. Then the silver layer on the PET film was divided into two electrically insulated portions by forming a scribed groove with a cutter knife at the central portion of the silver layer, thereby forming a pair of half cells. Another PET film bearing thereon a pair of half cells which was identical to that described immediately above except that the silver layer was divided into two half cells by a cut groove formed by mechanically cutting the silver layer with a cutting tool was prepared. Each of the PET films thus obtained was oxidative-chlorinated with 36 mM hydrochloric acid and aqueous solution of 16 mM potassium dichromate for about 60 seconds, was removed of the masking films on the end portions, and then washed with water and dried, whereby a film-like silver-silver chloride electrode pair was obtained.

An acetone solution containing 10% by weight of cellulose acetate (39.4% degree of acetylation, produced by Eastman Chemical), and 5% by weight of polyethylene glycol (average molecular weight 400) was coated on the silver chloride portion to form a protective layer (to be interpreted to be one of the ion selective layers in this specification), which was 3 μm thick in dry state. A double-sided adhesive tape (PET film base) provided with a pair of 3 mm openings for permitting the sample liquid and the reference liquid to be deposited onto the respective half cells was applied to the protective layer or the ion selective layer of the Cl⁻ ion-selective electrode pair thus obtained as a mask for mounting thereon a porous bridge, and a spun yarn of PET fiber was stretched between the openings as the porous bridge. Then a duplicativity test in measuring Cl⁻ ion activity was carried out.

In the case of the ion selective electrode pair in accordance with the prior art, i.e., the ion selective electrode pair having a scribed groove, the mask for mounting the porous bridge sometimes floated off the surface of the electrode pair after once being fixedly applied thereto, and therefore the sample liquid and/or the reference liquid sometimes flowed out to give anomalous measured values.

On the other hand, in the case of the ion selective electrode pair in accordance with the present invention, i.e., the ion selective electrode pair having a cut groove, the mask for mounting the porous bridge was firmly bonded to the surface of the ion selective electrode pair, and no anomalous measured values were obtained in Cl⁻ ion activity measurement.

A similar result was obtained when the groove (scribed one or cut one) was formed after the oxidative-chlorination.

EXAMPLE 3

A 3% aqueous solution of NaCl was coated on a film-like silver-silver chloride electrode pair obtained in a manner identical to that in Example 2 and then dried in a gentle stream of hot air at about 150° C. for three minutes, whereby an electrolyte layer (without binder) weighting was 1.2 g/m² was formed. Thereafter, an ion selective layer coating liquid having the following composition was coated on the electrolyte layer to form a layer 25 μm thick in a normal manner, thereby preparing an ion selective electrode pair for analyzing Na⁺ ion.

Composition of the Ion Selective Layer Coating Liquid vinyl chloride-vinyl acetate copolymer: 0.9 g
dicresyl phenyl phosphate: 1.2 g
methylmonencin: 0.1 g
tetraphenyl sodium borate: 2 mg
methyl ethyl ketone: 5 mg
1% SH510 (polysiloxane) solution in methyl ethyl ketone: 50 mg The ion selective electrode pair thus obtained was evaluated in a manner identical to that in Example 2. In the case of the ion selective electrode having a scribed groove, the mask for mounting the porous bridge was apt to float after once being bonded to the electrode pair, and therefore anomalous measured values were sometimes obtained in ion activity measurement. On the other hand, in the case of the ion selective electrode having a cut groove in accordance with the present invention, the mask for mounting the porous bridge was firmly bonded to the ion selective electrode and accordingly no anomalous measured values were obtained.

EXAMPLE 4

A 3% aqueous solution of KCl was coated on a film-like silver-silver chloride electrode pair obtained in a manner identical to that in Example 2 and then dried in a gentle stream of hot air at about 150° C. for three minutes, whereby an electrolyte layer (without binder) weighting of which was 1.3 g/m² was formed. Thereafter, an ion selective layer coating liquid having the following composition was coated on the electrolyte layer to form a layer 20 μm thick in an ordinal manner, thereby preparing an ion selective electrode pair for analyzing K⁺ ion.

Composition of the Ion Selective Layer Coating Liquid vinyl chloride-vinyl acetate copolymer: 0.9 g
dioctyl adipate: 1.2 g
valinomycin: 44 mg
tetrakis-p-chlorophenyl potassium borate: 18 mg
methyl ethyl ketone: 5 g
1% SH510 (polysiloxane) solution in methyl ethyl ketone: 50 mg
methyl ethyl ketone: 50 mg A hundred ion selective electrode pairs having a scribed groove and a hundred ion selective electrode pairs having a cut groove were thus prepared and were subjected to duplicativity test. In the case of the electrode pairs having a scribed groove, some of them exhibited electrical connection across the groove. On the other hand, in the case of the electrode pairs having a cut groove, none of them exhibited electrical connection across the groove. Further, duplicativity in measured value of the ion activity was not higher than CV 3% in the case of the ion selective electrode pairs having a cut groove in accordance with the present invention.

We claim:

1. A method of manufacturing an ion selective electrode pair comprising the steps of:
    forming a conductive layer on an insulating base;

dividing said conductive layer into at least two portions electrically isolated from each other by simultaneously cutting and removing at least a part of the material of the conductive layer with a cutting tool selected from the group consisting of a slotter tool bit, a fluting tool bit and a cutting-off cutter to form a groove; and then forming an ion selective layer on said conductive layer.

2. A method as defined in claim 1 in which said conductive layer is selected from the group consisting of conductive metals, conductive metal oxides and graphite.

3. A method as defined in claim 1 in which said conductive layer comprises graphite and a redox couple containing at least two kinds of redox couple salts.

4. A method as defined in claim 1 in which said conductibe layer comprises silver and said layer of water-insoluble salt comprises silver halide.

5. A method as defined in claim 1 in which at least one of said two portions of the conductive layer has an area exhibiting a certain potential when a sample liquid is brought into contact with the ion selective layer.

6. The method of claim 1 wherein the conductive layer is formed from a conductive metal and which further comprises forming a layer of a water-insoluble salt of the metal of the conductive layer on the conductive layer prior to cutting the groove.

7. The method of claim 1 further comprising forming a redox couple layer containing at least two kinds of redox couple salts on the conductive layer prior to cutting the groove.

8. the method of claim 1 wherein the conductive layer comprises a conductive metal and which further comprises, prior to cutting said groove, forming a layer of a water-insoluble salt of the conductive metal on the conductive layer and then forming a layer of a water-soluble salt having an anion in common with the water-insoluble salt on the layer of the water-insoluble salt.

9. The method of claim 1 wherein the conductive layer comprises silver, and which further comprises, after cutting the groove, forming a silver halide layer by oxidative halogenation of the silver layer and then forming the ion selective layer.

* * * * *